US009883993B2

(12) United States Patent
Gershon et al.

(10) Patent No.: US 9,883,993 B2
(45) Date of Patent: Feb. 6, 2018

(54) NOTCH FILTER COATINGS FOR USE IN SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/082,656

(22) Filed: Mar. 28, 2016

(65) Prior Publication Data

US 2017/0065503 A1 Mar. 9, 2017

Related U.S. Application Data

(60) Provisional application No. 62/213,703, filed on Sep. 3, 2015.

(51) Int. Cl.
*A61K 8/27* (2006.01)
*A61K 8/02* (2006.01)
*A61K 8/29* (2006.01)
*A61K 8/25* (2006.01)
*A61K 8/21* (2006.01)
*A61Q 17/04* (2006.01)
*A61K 8/26* (2006.01)
*A61K 8/19* (2006.01)

(52) U.S. Cl.
CPC .............. *A61K 8/27* (2013.01); *A61K 8/0241* (2013.01); *A61K 8/19* (2013.01); *A61K 8/21* (2013.01); *A61K 8/25* (2013.01); *A61K 8/26* (2013.01); *A61K 8/29* (2013.01); *A61Q 17/04* (2013.01); *A61K 2800/412* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| | | | |
|---|---|---|---|
| 3,761,261 A | 9/1973 | Ono et al. | |
| 3,863,007 A | 1/1975 | Warner, Jr. | |
| 4,549,195 A * | 10/1985 | Bluzer | H01L 21/471 257/442 |
| 5,011,782 A * | 4/1991 | Lamb | H01L 31/02168 136/255 |
| 5,147,125 A | 9/1992 | Austin | |
| 5,223,250 A | 6/1993 | Mitchell | |
| 5,441,726 A | 8/1995 | Mitchnick | |
| 5,534,056 A | 7/1996 | Kuehnle | |
| 6,419,909 B1 | 7/2002 | Lorant | |
| 9,056,063 B2 | 6/2015 | Hanson | |
| 9,144,535 B1 | 9/2015 | Daly et al. | |
| 9,144,536 B1 | 9/2015 | Daly et al. | |
| 2002/0122832 A1 | 9/2002 | Hanke | |
| 2003/0102099 A1 | 6/2003 | Yadav | |
| 2004/0209081 A1 | 10/2004 | Hagihara | |
| 2005/0008861 A1 | 1/2005 | Yadav et al. | |
| 2005/0048010 A1 | 3/2005 | Kliss | |
| 2005/0208005 A1 | 9/2005 | Giroud | |
| 2005/0227063 A1 | 10/2005 | Lawandy | |
| 2006/0228310 A1 | 10/2006 | Lyth | |
| 2006/0270053 A1 * | 11/2006 | Tilak | G01N 27/4141 436/143 |
| 2007/0280895 A1 * | 12/2007 | Weimer | A61K 8/11 424/59 |
| 2008/0220026 A1 | 9/2008 | Maltra | |

(Continued)

FOREIGN PATENT DOCUMENTS

CN 103071535 A 5/2013
EP 1889810 A1 2/2008

(Continued)

OTHER PUBLICATIONS

Ultraviolet radiation and the INTERSUN Programme [online]. WHO, Nov. 2003 [retrieved on Jun. 8, 2017]. Retrieved from the internet <http://www.who.int/uv/uv_and_health/en/>.*
Thokozane Moses Sithole, Synthesis and characterization of $MB_xO_y$:Eu (M=Ca, Sr, Ba) phosphors and $TiO_2$ semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped $YAlO_3$ Nanocrystals, J. Phys. Chem. C 2008, 112, 15071-15074.
Refractive index of ZnO (Zinc oxide)—Bond-o, http://refractiveindex.info/?shelf=main&book=ZnO&page=Bond-o, Mar. 25, 2016.

(Continued)

*Primary Examiner* — Richard A Schnizer
*Assistant Examiner* — Katherine Peebles
(74) *Attorney, Agent, or Firm* — Ryan, Mason & Lewis, LLP

(57) ABSTRACT

Notch filter coatings for use in sunscreen applications are provided herein. An exemplary composition includes multiple zinc oxide particles suspended within a medium forming sunscreen composition; and a combination of multiple notch filter coating materials individually applied as a distinct layer to each of the multiple zinc oxide particles to create a multi-layered structure surrounding each of the multiple zinc oxide particles within the sunscreen composition, wherein the multi-layered structure: reflects light at a user-determined wavelength range based on the wavelength range at which each of the multiple notch filter coating materials reflects light; and allows wavelengths of light (i) within at least a portion of the ultraviolet spectrum and (ii) outside of the user-determined wavelength range to be absorbed by the multiple zinc oxide particles.

10 Claims, 2 Drawing Sheets

(56) References Cited

U.S. PATENT DOCUMENTS

| | | | |
|---|---|---|---|
| 2009/0022765 | A1 | 1/2009 | Chung |
| 2009/0258072 | A1 | 10/2009 | Schlossman |
| 2009/0258230 | A1 | 10/2009 | Schlossman |
| 2010/0008872 | A1 | 1/2010 | Katusic |
| 2010/0055138 | A1 | 3/2010 | Margulies |
| 2011/0268678 | A1* | 11/2011 | Armstrong ............... A61K 8/35 424/60 |
| 2013/0216834 | A1 | 8/2013 | Hashimoto |
| 2014/0142213 | A1 | 5/2014 | Weiss |
| 2015/0283059 | A1 | 10/2015 | Nagare |
| 2016/0082513 | A1 | 3/2016 | Niedermeyer |

FOREIGN PATENT DOCUMENTS

| | | |
|---|---|---|
| JP | 09059591 A | 3/1997 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2012046204 A1 | 4/2012 |
| WO | 2014049139 A1 | 4/2014 |
| WO | 2014077189 | 5/2014 |
| WO | 2016020168 A1 | 2/2016 |

OTHER PUBLICATIONS

Refractive index of SiO2 (Silicon dioxide, Silica, Quartz)—Malitson, http://refractiveindex.info/?shelf=main&book=SiO2&page=Malitson, Mar. 25, 2016.

Schubert et al., Design of multilayer antireflection coatings made from co-sputtered and low-refractive-index materials by genetic algorithm. Optics Express vol. 16, No. 8, 2008.

Law et al., ZnO—Al2O3 and ZnO—TiO2 Core-Shell Nanowire Dye-Sensitized Solar Cells. J. Phys. Chem. B 2006, 110, 22652-22663.

Pu et al., Core/shell structured ZnO/SiO2 nanoparticles: Preparation, characterization and photocatalytic property. Applied Surface Science 257 (2010) 393-397.

Mantz et al., Progress in Organic Coatings 47 (2003) 432-442, "A multiple-scattering model analysis of zinc oxide pigment for spacecraft thermal control coatings."

Song et al., Toxicology Letters 199 (2010) 389-397, "Role of the dissolved zinc io and reactive oxygen species in cytotoxicity of ZnO nanoparticles."

Bohren et al., "Absorption and Scattering of Light by Small Particles", Wiley-VCH, © 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation."

NanoComposix, Silver Nanoparticles: Optical Properties, http://nanocomposix.com/pages/silver-nanoparticles-optical-properties, Apr. 20, 2016.

Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011—Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152, Dec. 7, 2016.

Luo et al., Facile synthesis of composition-tuned ZnO/ZnxCd1-xSe nanowires for photovoltaic applications, Nanoscale Research Letters (2015) 10:181.

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Naylor et al. "Sunscreens," accessed 2017, http://telemedicine.org/sundam/sundam2.4.2.html.

Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.

Tariq Jan, et al. Sn Doping Induced Enhancement in the Activity of ZnO Nanostructures Against Antibiotic Resistant *S. aureus* Bacteria; Int J. Nanomedicine, vol. 8, pp. 3679-3687; Published online Sep. 30, 2013.

Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

* cited by examiner

NOTCH FILTER COATINGS FOR USE IN SUNSCREEN APPLICATIONS

CROSS-REFERENCE TO RELATED APPLICATIONS

The present application claims priority to U.S. Provisional Application Ser. No. 62/213,703, filed Sep. 3, 2015, incorporated by reference herein.

The present application is also related to a commonly assigned U.S. application entitled "Nitride-Based Nanoparticles for Use in Sunscreen Applications," identified by Ser. No. 15/082,632, and filed on even date herewith, the disclosure of which is incorporated by reference herein in its entirety.

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

Further, it is noted that some amount of high-energy light (for example, light within a wavelength range of approximately 270 nm to approximately 300 nm) is needed by the human body for producing vitamin D (which is useful, for example, in calcium absorption and bone growth). Accordingly, while existing sunscreen compositions are capable of blocking portions of UV light from passing through the composition to be absorbed by the skin of the user, such compositions simultaneously preclude the UV light responsible for aiding vitamin D production to be absorbed by the skin.

SUMMARY

In one embodiment of the present invention, notch filter coatings for use in sunscreen applications are provided. An exemplary method can include selecting a combination of multiple notch filter coating materials to be applied to each of multiple zinc oxide particles within a sunscreen composition, wherein said selecting is based on a wavelength range at which each of the notch filter coating materials reflects light. The method can also include individually applying each of the selected notch filter coating materials as a distinct layer to each of the multiple zinc oxide particles to create a multi-layered structure surrounding each of the multiple zinc oxide particles within the sunscreen composition. In such a method, the multi-layered structure reflects light at a user-determined wavelength range based on the selected combination of notch filter coating materials, and allows wavelengths of light (i) within at least a portion of the ultraviolet spectrum and (ii) outside of the user-determined wavelength range to be absorbed by the multiple zinc oxide particles.

In another embodiment of the invention a composition can include multiple zinc oxide particles suspended within a medium forming sunscreen composition; and a combination of multiple notch filter coating materials individually applied as a distinct layer to each of the multiple zinc oxide particles to create a multi-layered structure surrounding each of the multiple zinc oxide particles within the sunscreen composition, wherein the multi-layered structure: reflects light at a user-determined wavelength range based on the wavelength range at which each of the multiple notch filter coating materials reflects light; and allows wavelengths of light (i) within at least a portion of the ultraviolet spectrum and (ii) outside of the user-determined wavelength range to be absorbed by the multiple zinc oxide particles.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes zinc oxide compositions, methods of fabrications thereof and methods of use thereof. Specifically, at least one embodiment of the invention includes notch filter coatings for use in sunscreen applications.

As further detailed herein, one or more embodiments of the invention include generating ZnO (or nitride-based) compositions and methods of use thereof for permitting a specific range (or "windows") of light (radiation) to pass through a ZnO composition such that the specific range of light can be absorbed by the skin of a human user. For example, at least one embodiment of the invention can include generating a ZnO composition that allows radiation at 276 nm (which is the wavelength that facilitates Vitamin D absorption in the skin) to pass through the composition to be absorbed by the skin, while blocking harmful UV radiation at other wavelengths.

At least one embodiment of the invention includes applying one or more notch filter coatings to ZnO particles to create a sunscreen composition. As used herein, a "notch filter" refers to as a band-stop filter with a narrow stopband. That is, a notch filter that is constituted for a specific wavelength range prevents light in that specific wavelength range from being absorbed by the ZnO particles of a sunscreen composition (that is, the layers and/or filters applied to the ZnO particles reflect the light in that specific wavelength range), such that the light in that specific wavelength range can pass through the sunscreen composition to be absorbed by the skin.

Figure 1:
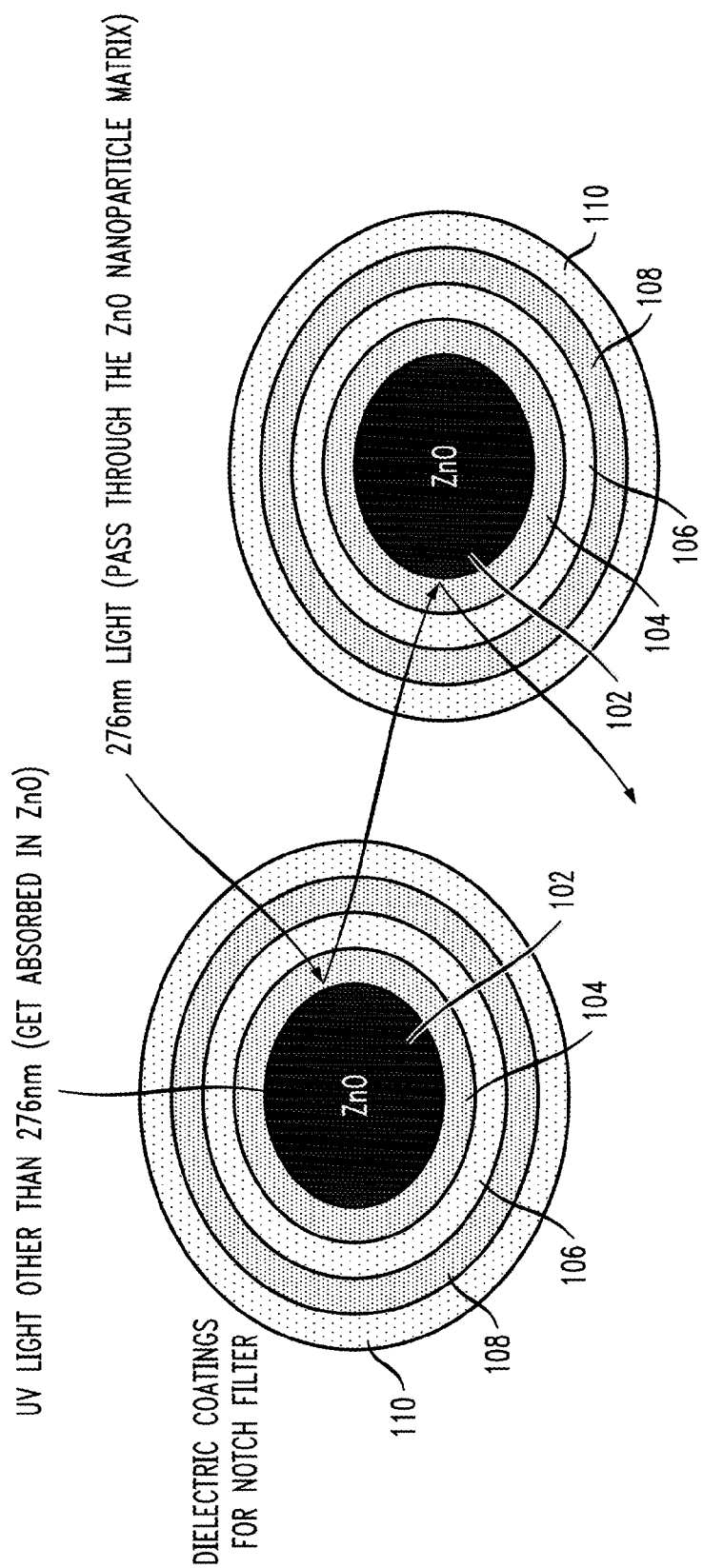
FIG. 1 is a diagram illustrating ZnO particles that include notch filter coatings, according to an exemplary embodiment of the invention.

FIG. 1 is a diagram illustrating ZnO particles that include notch filter coatings, according to an exemplary embodiment of the invention. By way of illustration, FIG. 1 depicts a multi-layered coating approach, which results in a narrow (desired) range of reflection. Specifically, FIG. 1 depicts a multi-layered structure of dielectric filters (layers/filters 104, 106, 108, and 110), that serves as a high-reflection coating for a Vitamin D relevant wavelength, applied to ZnO particles 102. As noted in FIG. 1, in the illustrated example embodiment, the relevant wavelength is 276 nm. Alternatively, at least one embodiment of the invention can include generating a multi-layered coating that serves as a high-reflection coating for light in the wavelength range of approximately 276-300 nm.

As illustrated, in the example embodiment depicted in FIG. 1, UV light other than light at 276 nm is absorbed by the ZnO particles (102), while 276 nm light is reflected (by the filters/layers) and passes through the ZnO nanoparticle matrix as a result of the multi-layered structure of dielectric filters (layers/filters 104, 106, 108, and 110) applied to the ZnO particles 102. The filters and/or layers can include materials with refractive index contrast. By way of example, in at least one embodiment of the invention, the thickness of a layer is one-quarter of the specific light wavelength inside the material for normal incidence light. For a film (that is, material) comprising small particles, the exact thickness can be determined via a Mie scattering model to enhance the reflection from all angles throughout the film.

In one or more embodiments of the invention, dielectric coating materials utilized for optical notch filters (such as depicted by layers/filters 104, 106, 108, and 110 in FIG. 1) can include, for example, zinc selenide (ZnSe), magnesium fluoride ($MgF_2$), silicon dioxide ($SiO_2$), silicon nitride (SiN), aluminum oxide ($Al_2O_3$), titanium dioxide ($TiO_2$), and/or hafnium(IV) oxide ($HfO_2$). By way of further example, any material that is transparent to UV light and can be easily deposited can be candidates to serve as filter materials.

In one or more embodiments of the invention, a combination of any two or more materials detailed in the above paragraph can be utilized in a multi-layered approach. In an example embodiment, the thickness of the layers in such an approach can include the wavelength divided by the refractive index of the material, and then further dividing that resultant number by four. The layer sequence can be arranged in a way such that the reflected light from each interface constructively interferes with one another to maximize reflection and minimize transmission.

Additionally, in at least one embodiment of the invention, dielectric filters can be formed by applying a conformal coating on ZnO particles using chemical vapor deposition (CVD), atomic layer deposition (ALD), solution processes, etc. Also, as further described in the above-noted related U.S. application entitled "Nitride-Based Nanoparticles for Use in Sunscreen Applications," identified by Ser. No. 15/082,632 the disclosure of which is incorporated by reference herein in its entirety, at least one embodiment of the invention can include utilizing, in lieu of ZnO particles, nitride based particles as a core material. Such nitride based particles can include, for example, gallium nitride (GaN) and/or indium gallium nitride (InGaN).

Figure 2:
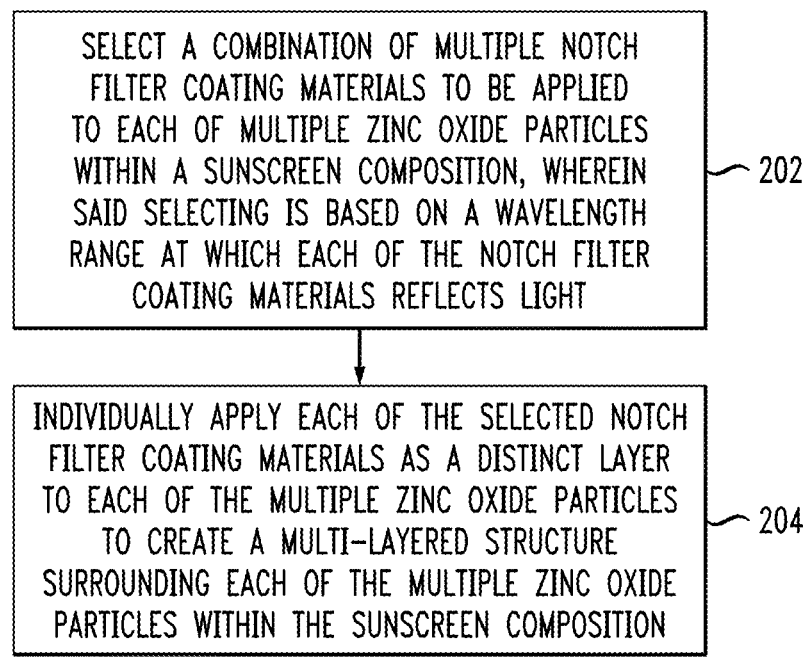
FIG. 2 is a flow diagram illustrating techniques according to an embodiment of the invention.

FIG. 2 is a flow diagram illustrating techniques according to an embodiment of the present invention. Step 202 includes selecting a combination of multiple notch filter coating materials to be applied to each of multiple zinc oxide particles within a sunscreen composition, wherein said selecting is based on a wavelength range at which each of the notch filter coating materials reflects light. The notch filter coating materials can include zinc selenide, magnesium fluoride, silicon dioxide, silicon nitride, aluminum oxide, titanium dioxide, and/or hafnium(IV) oxide.

Additionally, in one or more embodiments of the invention, the thickness of each of the notch filter coating materials is determined by the Mie scattering model such that reflection of the specific wavelength of light corresponding with the given notch filter coating material is maximized.

Step 204 includes individually applying each of the selected notch filter coating materials as a distinct layer to each of the multiple zinc oxide particles to create a multi-layered structure surrounding each of the multiple zinc oxide particles within the sunscreen composition. Additionally, the multi-layered structure reflects light at a user-determined wavelength range based on the selected combination of notch filter coating materials, and allows wavelengths of light (i) within at least a portion of the ultraviolet spectrum and (ii) outside of the user-determined wavelength range to be absorbed by the multiple zinc oxide particles.

The user-determined wavelength range can include a range between approximately 276 nanometers and 300 nanometers. Additionally, in one or more embodiments of the invention, the user-determined wavelength range can include 276 nanometers. Also, in at least one embodiment of the invention, the applying step can include applying each of the selected notch filter coating materials as a distinct layer to each of the multiple zinc oxide particles via at least one of (i) chemical vapor deposition, (ii) atomic layer deposition, and (iii) a solution process.

Also, an additional embodiment of the invention includes a composition that includes multiple zinc oxide particles suspended within a medium forming sunscreen composition; and a combination of multiple notch filter coating materials individually applied as a distinct layer to each of the multiple zinc oxide particles to create a multi-layered structure surrounding each of the multiple zinc oxide particles within the sunscreen composition. Such a multi-layered structure reflects light at a user-determined wavelength range based on the wavelength range at which each of the multiple notch filter coating materials reflects light. Additionally, such a multi-layered structure allows wavelengths of light (i) within at least a portion of the ultraviolet spectrum and (ii) outside of the user-determined wavelength range to be absorbed by the multiple zinc oxide particles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, generating a ZnO composition that allows radiation at 276 nm to pass through the composition to be absorbed by the skin, while blocking harmful UV radiation at other wavelengths.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A process of making a sunscreen composition, comprising:
    selecting a combination of multiple notch filter coating materials to be applied to each of multiple zinc oxide particles within the sunscreen composition; and
    individually applying each of the selected notch filter coating materials as a distinct layer to each of the multiple zinc oxide particles to create a multi-layered structure surrounding each of the multiple zinc oxide particles within the sunscreen composition, wherein the multi-layered structure:
        reflects light at a wavelength of 276 nanometers based on the selected combination of notch filter coating materials; and
        allows wavelengths of light within the ultraviolet spectrum, with the exception of the wavelength of 276 nanometers, to be absorbed by the multiple zinc oxide particles, and allows radiation at 276 nanometers to pass through the sunscreen composition to be absorbed by skin and ultraviolet light other than at 276 nanometers is absorbed by the sunscreen.

2. The method of claim 1, wherein the thickness of each of the notch filter coating materials is determined by the Mie scattering model such that reflection of the specific wavelength of light corresponding with the given notch filter coating material is maximized.

3. The method of claim 1, wherein the multiple notch filter coating materials comprise at least zinc selenide.

4. The method of claim 1, wherein the multiple notch filter coating materials comprise at least magnesium fluoride.

5. The method of claim 1, wherein the multiple notch filter coating materials comprise at least silicon dioxide.

6. The method of claim 1, wherein the multiple notch filter coating materials comprise at least silicon nitride.

7. The method of claim 1, wherein the multiple notch filter coating materials comprise at least aluminum oxide.

8. The method of claim 1, wherein the multiple notch filter coating materials comprise at least titanium dioxide.

9. The method of claim 1, wherein the multiple notch filter coating materials comprise at least hafnium(IV) oxide.

10. The method of claim 1, wherein said applying comprises individually applying each of the selected notch filter coating materials as a distinct layer to each of the multiple zinc oxide panicles via at least one of (i) chemical vapor deposition, (ii) atomic layer deposition, and (iii) a solution process.

* * * * *